United States Patent [19]

Legay et al.

[11] Patent Number: 5,330,510
[45] Date of Patent: Jul. 19, 1994

[54] PACEMAKER WITH PATIENT EFFORT-CONTROLLED FREQUENCY

[75] Inventors: Thierry Legay, Fontenay Les Briis; Alain Ripart, Gif-Sur-Yvette, both of France

[73] Assignee: ELA Medical, Montrouge, France

[21] Appl. No.: 995,050

[22] Filed: Dec. 22, 1992

[30] Foreign Application Priority Data

Dec. 31, 1991 [FR] France .................... 91 16368

[51] Int. Cl.$^5$ ............................ A61N 1/365
[52] U.S. Cl. ...................................... 607/19
[58] Field of Search ..................... 607/18, 19

[56] References Cited

U.S. PATENT DOCUMENTS

| | | | |
|---|---|---|---|
| 3,593,718 | 7/1971 | Kramer | 128/429 P |
| 4,140,132 | 2/1979 | Dahl | 128/419 PG |
| 4,201,219 | 5/1980 | Gonzalez | 128/419 PG |
| 4,653,326 | 3/1987 | Dand et al. | |
| 4,771,780 | 9/1988 | Sholder | 128/419 B |
| 4,926,863 | 5/1990 | Alt | 128/419 PG |
| 5,012,316 | 4/1991 | Silvermint | 357/26 |
| 5,014,700 | 5/1991 | Alt | 128/419 PG |
| 5,014,702 | 5/1991 | Alt | 128/419 PG |
| 5,014,703 | 5/1991 | Alt | 128/419 PG |
| 5,014,704 | 5/1991 | Alt | 128/419 PG |
| 5,016,632 | 5/1991 | Hoegnelid et al. | 128/419 PG |
| 5,031,614 | 6/1991 | Alt | 128/419 PG |
| 5,031,615 | 6/1991 | Alt | 128/419 PG |
| 5,233,984 | 8/1993 | Thompson | 607/18 |

FOREIGN PATENT DOCUMENTS

| | | | |
|---|---|---|---|
| 0080348 | 1/1983 | European Pat. Off. | A61N 1/36 |
| 0414928 | 6/1991 | European Pat. Off. | A61N 1/36 |
| 2838854 | 10/1980 | Fed. Rep. of Germany | A61B 5/00 |
| 0149572 | 9/1985 | France | G01P 15/08 |
| 9008570 | 9/1980 | World Int. Prop. O. | A61N 1/00 |

OTHER PUBLICATIONS

Anderson, Kenneth M., "Research Leads To Major Breakthrough In Rate-Responsive Pacemaking", Sensor Pacing Oct. 1986, pp. 89–93.

Anderson, Kenneth, "An Activity Sensor To Control Heart Rate", Implatable Sensors For Closed-Loop Prosthetic Systems, Mt. Kisco, N.Y., Futura Publishing, Inc., 1985 pp. 243–250.

Primary Examiner—William E. Kamm
Attorney, Agent, or Firm—Davis Hoxie Faithfull & Hapgood

[57] ABSTRACT

A pacemaker with patient effort-controlled stimulation frequency that responds to a control parameter. Accelerometers (1) with capacity variation are placed on a substratum. Each of the accelerometers is sensitive in one direction of a Cartesian coordinate system. The output of the accelerometers are combined and integrated over a small time constant to produce a signal representative of the patient's metabolic power exerted. The signal is then used to control the stimulation frequency of the pacemaker. The integration may be based on the sum of the absolute value of the acceleration signals or the square root of the sum of the squares of the acceleration signals.

70 Claims, 3 Drawing Sheets

PACEMAKER WITH PATIENT EFFORT-CONTROLLED FREQUENCY

BACKGROUND OF THE INVENTION

This invention relates to a pacemaker with patient effort-controlled frequency, more particularly to a rate adaptive pacemaker that adjusts the stimulating frequency in accordance with the patient's physical effort.

It is known that the effort exerted by a patient can be monitored based on a measure of acceleration along an axis, e.g., a vertical or antero-posterior axis. An accelerometer placed on the patient's trunk provides a signal that enables one to obtain an approximation of the energy expended for the patient's dynamic efforts. There is a good correlation between the integral of the absolute value of the signal of acceleration along the vertical axis, for instance, and the energy expended by the patient. Computation of this integral for set periods of time provides an image of the power supplied by the patient in dynamic efforts, which can be selected as a control parameter for controlling the heart rate. See, e.g., U.S. Pat. No. 4,926,863, which describes a rate-responsive cardiac pacemaker with the pacing frequency controlled based on acceleration measured along an antero-posterior axis.

SUMMARY OF THE INVENTION

It is an object of this invention to provide improved methods and apparatus for controlling a pacemaker pacing frequency as a function of the patient's efforts. It is another object to provide a control parameter that is more representative of metabolic power than the prior known effort-controlled pacemakers. It is yet another object to provide improved algorithms for controlling the pacing energy in response to an acceleration based control parameter.

It is a further object of this invention to provide a patient an effort controlled pacemaker that responds to a control parameter and information that is coherent at all times, even if the pacemaker box turns or shifts after implantation. It is another object to provide a particularly reliable control parameter even if the pacemaker box rotates.

Broadly, the present invention is directed to a pacemaker with a pacing frequency that is controlled by the patient's effort, according to a parameter computed from the acceleration measured at the level of the patient's trunk. One aspect of the invention concerns methods and apparatus for measuring the acceleration along two axes that are perpendicular to one another and measuring the acceleration along a third axis perpendicular to the two previous axes, wherein the two axes perpendicular to one another are parallel to the flat surface of the implanted pacemaker box.

Accordingly, the control parameter is derived as a function of the values of the signals representing the acceleration along the three axes. The control parameter is thus related to the metabolic power used up by the patient in the course of the patient's efforts producing those signals.

In one embodiment, the control parameter is the integral, computed for a predetermined period of time, of the sum of the absolute values of the signals representing the acceleration along the three axes. In an alternate embodiment, the control parameter is the integral, computed for a predetermined period of time, of the square root of the sum of the squares of the signals representing the acceleration along the three axes.

The acceleration measuring devices are comprised, for each of said axes, of an accelerometer (also referred to as an accelerometric sensor) that is sensitive to motion in only one direction. The accelerometer may be based on capacity variation; but other phenomenon that produce a variable electrical signal in response to motion in a given direction may be used.

Preferably, the accelerometer is comprised of a flat substratum, the accelerometer being sensitive in one direction contained in the plane of the substratum. Two accelerometers may be mounted on the same substratum and oriented so as to be sensitive in two perpendicular directions, and the third accelerometer is provided to be sensitive in a direction perpendicular to the plane of said substratum. The third accelerometer may be mounted in the plane of substratum containing the two accelerometers. The third accelerometer is preferably mounted on that substratum, thereby providing a conveniently small package for insertion in a pacemaker box.

The apparatus of the present invention preferably includes an integrating unit that is highly constant in time and which produces an output signal in digital form. Preferably, the integrating unit comprises an integrator which generates a fast ramp with a time constant of a few milliseconds, a reference voltage comparator, a monostable circuit issuing a pulse at each flip of the comparator, and a counter that counts pulses, the count of which is an output signal in digital form.

A pacemaker microprocessor is adapted to receive and use the digital output signal from the counter to determine the controlled heart rate in accordance with a suitably selected protocol or rate control algorithm responsive to the digital signal control parameter.

BRIEF DESCRIPTION OF THE DRAWINGS

Further features and advantages of the invention will be apparent upon consideration of the following detailed description of preferred embodiments of this invention, taken in conjunction with the accompanying drawings, in which like reference characters refer to like parts throughout, and in which.

DETAILED DESCRIPTION OF THE INVENTION

Figure 1:
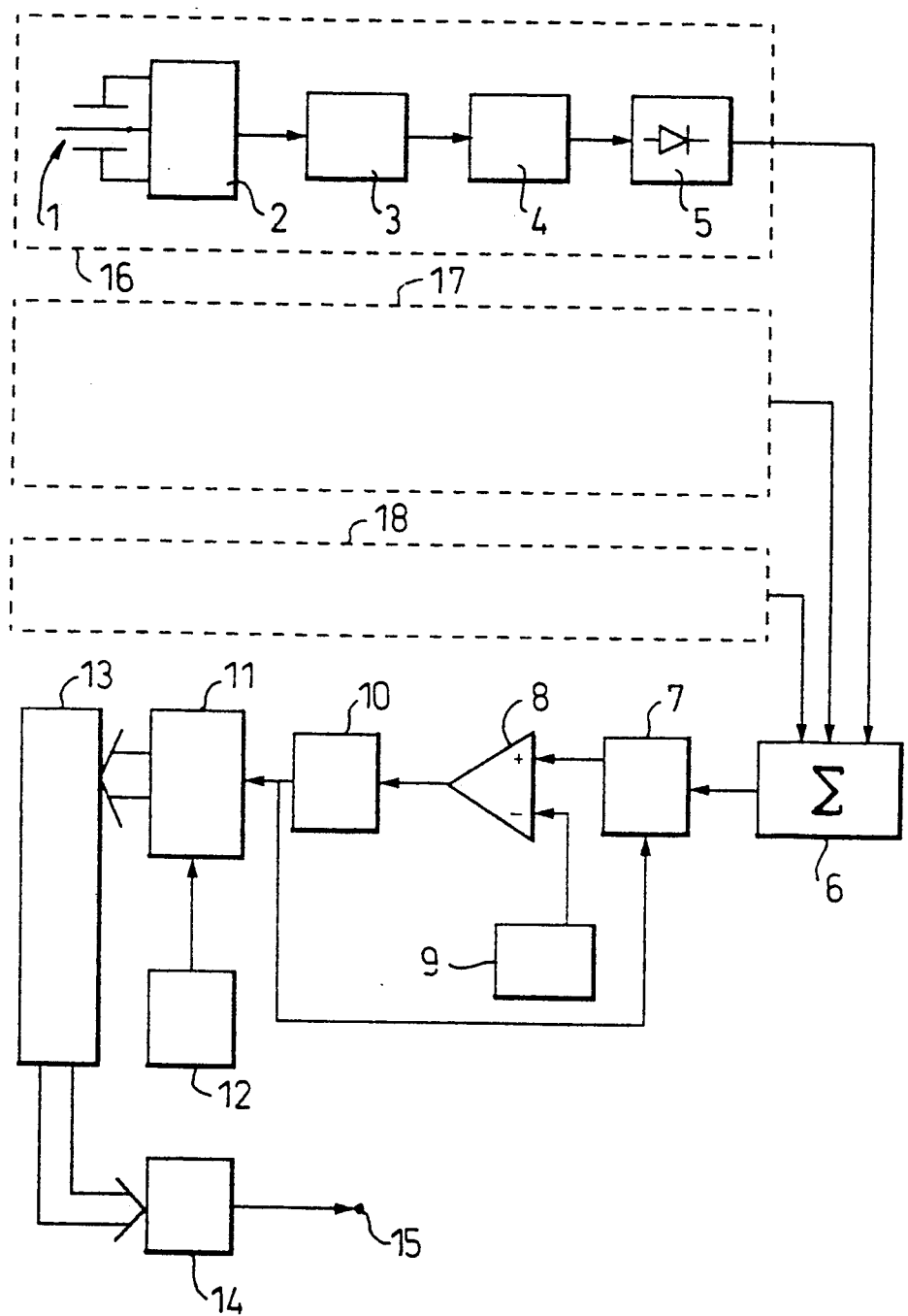
FIG. 1 is a symbolic circuit diagram for measuring the metabolic power from acceleration sensors along three orthogonal axes, and generating frequency controlled stimulus pulses, the control parameter being the integral of the sum of the absolute values of the signals representing the acceleration along said axes.
Figure 3:
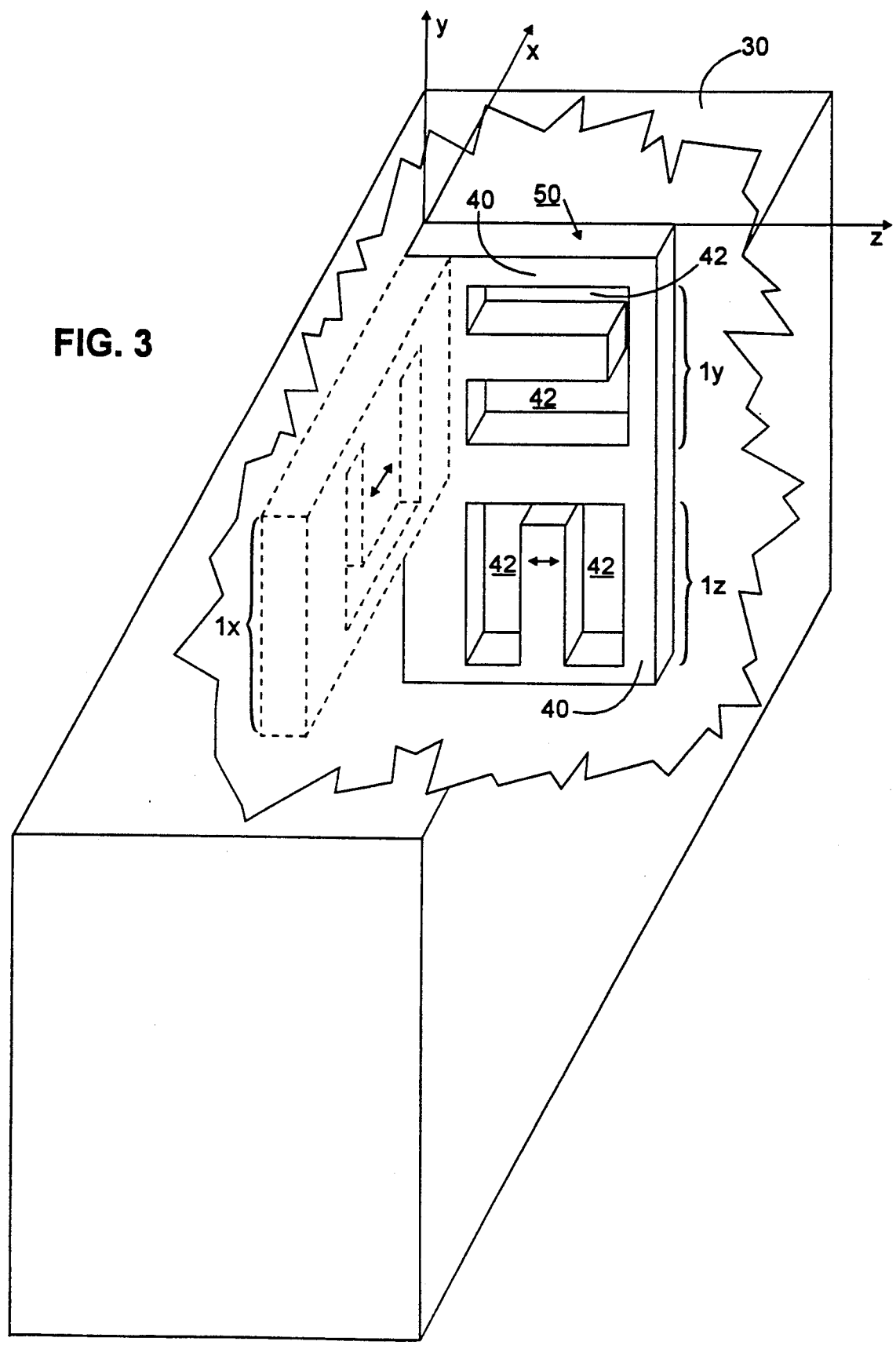
FIG. 3 is an elevated perspective, partial cutaway, view of the acceleration sensors inside a pacemaker box according to a preferred embodiment of the present invention.

With reference to FIGS. 1 and 3 in a preferred embodiment of the present invention, three orthogonal axes are provided for measurement of the acceleration: a horizontal antero-posterior axis x, a vertical axis y, and a lateral axis z. For each of these axes, a series of electronic modules is provided, respectively illustrated as modules 16, 17, 18. Each series comprises five modules including an accelerometric sensor 1, an amplifier 2, a low-pass filter 3, a high-pass filter 4, and a full-wave rectifier 5. A letter suffix is used when referring to a specific axis, the letters being omitted for general discussions.

Accelerometric sensor 1 is preferably of the capacitive type, i.e., with an output capacity variation. Preferably, sensor 1 is micro-machined on a silicon substratum, for instance, having a motion sensitive axis in a given direction in a plane of motion as indicated by the double arrows for sensors 1X, 1Y, and 1Z on FIG. 3.

Amplifier 2 produces a voltage output variation in response to the capacity variation output of sensor 1, which is referred to as the acceleration signal. Amplifier 2 may be configured to produce a typical output of 270 mV/g, where g is the acceleration due to gravity.

Low-pass filter 3 is provided for eliminating the interference in the acceleration signal picked up by sensor 1. Filter 3 has a cut-off frequency of a few Hz, typically 6 Hz.

High-pass filter 4 provides a cut-off frequency below 1 Hz, typically of 0.7 Hz, for eliminating the static from the earth's gravitational field.

Full-wave rectifier 5 provides the absolute value of the filtered acceleration signal.

For each of the three axes x, y, z (series 16, 17, and 18), the absolute value of the filtered acceleration signal is applied to an adder 6, which sums the signals. An integrator 7 receives the sum from adder 6 and generates a fast ramp, with a time constant of a few ms, typically 3.9 ms. The output of integrator 7 is applied to one input of a comparator 8. The reference input of comparator 8 receives a reference voltage from an adjustable reference voltage generating circuit 9.

The output of comparator 8 is connected to a monostable circuit 10, which supplies a pulse at each flip of comparator 8. The output of monostable circuit 10 is fed back to the reset input of integrator 7 and provided to the input of a counter 11.

The set of modules illustrated as 7 to 11 thus constitutes an integrator unit that is highly constant in time and has an output signal that is obtained directly in digital form. It functions as follows: Integrator 7 generates a fast ramp in a relatively short time. When the output of integrator 7 exceeds the reference voltage from circuit 9, comparator 8 flips over, i.e., changes state, triggering monostable circuit 10. This supplies a pulse which increments counter 11 and resets integrator 7. The process then begins again identically.

Adjusting the reference voltage input to comparator 8 enables the gain of the electronic circuit to be adjusted in order to adapt it to sensors of different sensitivity.

A clock 12 is provided to define the metabolic power computation time or measurement cycle, e.g., 1.5 s. In other words, every 1.5 s, the output of counter 11 is transferred to a buffer, latch or memory device (i.e., memorized in flip-flops) (not shown) by a microprocessor 13, and counter 11 is reset for a new measurement cycle. In this manner, the count acquired every 1.5 seconds is provided as a digital value Pmet, representative of a sum of the filtered acceleration signals produced by the patient on the three orthogonal axes. The value Pmet corresponds to the patient's metabolic power consumption and, hence, cardiac output requirements.

Microprocessor 13 acquires the measurement of the metabolic power Pmet and computes a heart rate using a linear relation:

$$Fc = (A)(Pmet) + FCbase$$

The parameter FCbase corresponds to the basic heart rate and is set (programmed) by the doctor in a conventional manner. The control slope A also is determined by the doctor, but can be automatically recomputed to adjust itself to suit the patient. See in this regard, copending and commonly assigned U.S. patent applications Ser. No. 07/813,204, filed Dec. 23, 1991, now U.S. Pat. No. and U.S. Ser. No. 07/813,905, filed Dec. 23, 1991, now U.S. Pat. No. 5,249,572 which are incorporated herein by reference in their entirety.

In determining the frequency of the heart pacing actually applied, the computed frequency F is only taken into account if it differs from the basic frequency by more than 6%. This allows for some hysteresis.

A pulse generating circuit 14 is provided, which is a specific integrated circuit. When appropriate, it receives from microprocessor 13 the width, amplitude and rate characteristics of the pacing pulses to be applied, and generates stimulating pulses which are applied to an electrode 15 of a pacing lead (cardiac catheter).

The control parameter obtained by the present invention is a function of the metabolic power Pmet used up by the patient during the effort. This power is computed by evaluating the energy expended by the patient over a set period of time, equal to 1.5 s in the example described. As noted, this period is set by clock 12. The expenditure of energy is obtained by integrating the sum of the absolute values of the acceleration signals measured along the axes of the accelerometric sensors.

Figure 2:
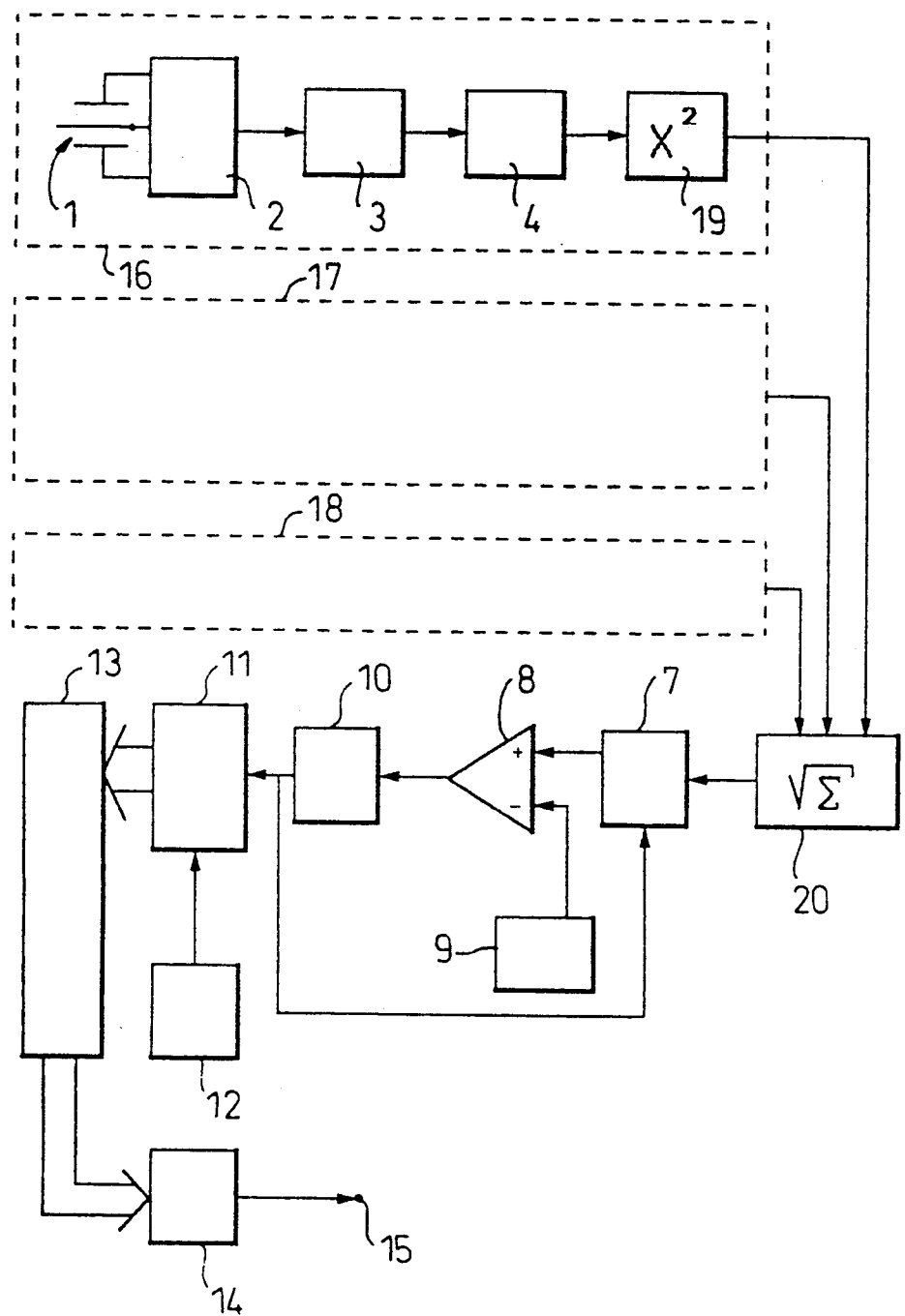
FIG. 2 is a symbolic circuit diagram similar to that in FIG. 1 except that the control parameter is the integral of the square root of the sum of the squares of said acceleration signals.

Referring to FIG. 2, an alternate embodiment of the invention is illustrated, in which the elements that are the same as the elements referred to in FIG. 1 are provided with the same reference numerals. The modifications with regard to the embodiment of FIG. 1 are as follows: In the embodiment illustrated in FIG. 2, full-wave rectifier 5 in each series 16, 17, and 18 is replaced by a square multiplier 19, and adder 6 is replaced by module 20. Whereas full-wave rectifier 5 provided the absolute value of the signal of acceleration along a given axis, square multiplier 19 provides the square of the signal of acceleration along that given axis. Thus, each of the series 16, 17, and 18 of electronic modules 1-4 and 19 produces the square of the signal of acceleration along its axis.

Whereas adder 6 (FIG. 1) produced the sum of the absolute values of the signals according to each of the three axes, electronic module 20 provides the square root of the sum of the squares of the signals of acceleration along each of the three axes.

In the embodiment illustrated in FIG. 2, the measurement of the acceleration is mathematically accurate. In the embodiment of FIG. 1, the measurement is approximate, and, in the event of rotation of the box, a measurement error of up to 25% can occur. However, such an error can be corrected by application of an algorithm automatically calibrating the relationship between the pacing rate Fc and the digital value Pmet, for instance. See, e.g., the aforementioned U.S. patents.

Referring to FIG. 3, acceleromatic sensors 1X, 1Y, 1Z are preferably in the form of integrated circuit devices disposed on the electronic circuit of the pacemaker, inside the pacemaker box 30. Together, accelerometric sensors 1 constitute a multi-dimensional accelerometer for improving the estimation of the power supplied by the patient in his/her dynamic effort. Sensor 1X is shown in phantom lines to illustrate differences between the three sensor structure already described and the two sensor structure described below.

An example of an accelerometric sensor susceptible of being used within the scope of the present invention is described in European patent No. 149,572 and U.S. Pat. No. 4,653,326. In one such structure a substratum 40, e.g., silicon, is provided with an aperture 42 through the substratum 40 which defines a flexible rod 45 extending from the substratum 40 into the aperture 42. The rod 45 has a length oriented in a direction (plane) parallel to the surface of the substratum, and susceptible to being deformed in a direction perpendicular to the direction in which it is oriented (in the direction of the double arrow) and parallel to the surface of the substratum 40. This rod 45 is thus capable of measuring, by sensing a capacity variation between the rod and the aperture surface(s), the component of acceleration in said direction perpendicular to the direction in which the rod is oriented.

With two sensors of this type sensitive in the perpendicular directions of a plane, and a third sensor sensitive in the direction perpendicular to this plane, the three sensors being disposed in said plane, or with equivalent sensors for measuring the accelerations in three perpendicular directions, all the components of acceleration are known.

The notable advantages of this disposition are:
- complete information on movement of the trunk, and consequently, a better approximation of the expenditure of energy per unit of time which yields a lower control parameter;
- insensitivity to the position of the pacemaker box and the position of the patient, because the measurement space is a three-dimensional Cartesian coordinate system; and
- a good signal-to-noise ratio.

In addition, the capacity variation accelerometers have the following features:
- excellent stability over time,
- a very low temperature drift with very high sensitivity, and
- minimum space requirements due to their very small active mass.

An accelerometric sensor of the type described is substantially flat; the direction in which the rod is oriented and the direction of detection of the accelerations are parallel to the surface of the substratum and perpendicular to one another. Referring to FIG. 3, as noted, two sensors 1Y and 1Z sensitive in two perpendicular directions can be disposed on or in the same flat substratum 40. The third sensor 1X (shown in phantom lines) may be disposed in the same plane (not shown), but must be sensitive in a direction perpendicular to this plane. The accelerometer embodying the invention is preferably constituted in the form of a chip, e.g., a silicon circuit element 50.

In some cases, i.e., for specific types of patients, the utilization of two accelerometric sensors is deemed sufficient. In this case, the two sensors preferably 1Y and 1Z (FIG. 3) detect accelerations along the patient's vertical axis and lateral axis (e.g., the series 17 and 18 of electronic modules 1-5 in FIG. 1). The information provided is substantially constant even if the pacemaker box turns subsequent to implantation, with the same restrictions as previously with regard to the processing of the signals. Accordingly, the case of two sensors is deemed as being within the scope of the invention.

One skilled interest will appreciate that the present invention can be practiced by other than the described embodiments, which are presented for purposes of illustration and not of limitation.

What is claimed is:

1. A pacemaker having a stimulation frequency controlled by the patient's effort according to a control parameter computer from the acceleration measured at the level of the patient's trunk, comprising first means for measuring acceleration along a first axis, second means for measuring acceleration along a second axis, and third means for measuring acceleration along a third axis, wherein the third axis is perpendicular to said first and second axes, and said first and second axes are perpendicular to one another and parallel to said flat surface, and wherein said first, second and third measuring means operate independently of one another; and
means for determining said control parameter for controlling the stimulation frequency as a function of the measured acceleration in said first, second and third axes.

2. The pacemaker as claimed in claim 1, wherein first, second and third measuring means further comprise first, second and third output signals corresponding to acceleration in the first, second and third axes respectively, and said determining means further comprise means for determining the control parameter as the integral, computed for a period of time, of the sum of the absolute values of said first, second and third signals.

3. The pacemaker as claimed in claim 2, wherein said determining means further comprises an integrator which generates a fast ramp signal with a time constant of a few milliseconds in response to said sum, a reference voltage comparator having an input for the ramp signal and an input for a reference signal, a first output state when the ramp is less than the reference signal and a second state when the ramp signal reaches the reference signal, wherein the comparator flips states in response to the ramp signal reaching the reference signal, a monostable circuit issuing a pulse at each flip of said comparator, and a counter for counting the number of pulses issued, wherein the count is said control parameter issuing an output signal in digital form.

4. The pacemaker as claimed in claim 1, wherein first, second and third measuring means further comprise first, second and third output signals corresponding to acceleration in the first, second and third axes respectively, and said determining means further comprises means for determining the control parameter as the integral, computed for a period of time, of the square root of the sum of the squares of said first, second and third signals representing the acceleration along said axes.

5. The pacemaker as claimed in claim 1, wherein the first, second and third acceleration measuring means are each comprised of an accelerometer that has a capacitance that varies in response to acceleration and an output signal that corresponds to said capacitance, wherein said accelerometer is sensitive to acceleration in one direction.

6. The pacemaker as claimed in claim 5, wherein two of said first, second and third measuring means are mounted on a same substratum and oriented so that their one directions of sensitivity are perpendicular.

7. The pacemaker as claimed in claim 6, wherein said other of the first, second and third measuring means has its one direction of sensitivity in a direction perpendicular to the plane of said substratum.

8. The pacemaker as claimed in claim 7, wherein said third measuring means is mounted in the plane of said substratum.

9. The pacemaker as claimed in claim 7, wherein said third measuring means is mounted on said substratum.

10. A method of providing a control parameter for a pacemaker having a stimulation frequency controlled by the patient's effort, comprising:
measuring first and second signals corresponding respectively to the acceleration, in response to patient effort, at the level of the patient's trunk along two axes perpendicular to one another;
measuring a third signal corresponding to the acceleration, in response to patient effort, at the level of the patient's trunk along a third axis perpendicular to said first, second and third signals are measured independently of one another;
computing a control parameter as a function of said first, second and third signals; and
providing said control parameter for controlling the pacemaker stimulation frequency;

11. The method of claim 15 wherein computing said control parameter further comprises processing the values of the first, second and third signals in relation to the metabolic power used up by the patient in the course of the effort producing said first, second and third signals.

12. The method of claim 11, wherein computing the control parameter further comprising obtaining the absolute values of said first, second, and third signals, summing said absolute values, and integrating said sum for a time period, said integrated sum at end of the time period being the control pacemaker.

13. The method of claim 11 wherein computing said control parameter further comprises squaring the value of each of the first, second and third signals, summing said square values, taking the square root of said sum, and integrating said square root for a time period, said integrated sum at the end of the time period being the control parameter.

14. The method of claim 10 wherein measuring each of the first second and third signals further comprises providing first, second and third accelerometers each of which is sensitive to motion in one direction and has an output signal corresponding to motion in said one direction, and orienting the first and second accelerometers along said two axes and orienting the third accelerometer along the third axis so that the first, second and third accelerometer outputs provide the first, second and third signals, respectively.

15. The method of claim 14 wherein providing the first, second an third accelerometer further comprises providing each said accelerometer with a capacity variation output that changes in response to acceleration.

16. The method of claim 14 wherein providing each of the first, second and third accelerometer further comprises providing an accelerometer made of a flat substratum, such that the one direction of sensitivity is contained in the plane of said substratum.

17. The method of claim 16 wherein providing the first, second and third accelerometer further comprises providing two of the first, second and third accelerometers mounted on or in the same substratum and oriented so as to be sensitive in perpendicular directions in said same substration plane.

18. The method of claim 17 further comprising mounting said other of the first, second and third accelerometers in the plane of said substratum.

19. A pacemaker with a stimulation frequency controlled by a control parameter related to the patient's effort, comprising:
a pacemaker box having a flat surface for implanting in a vertical orientation in a patient;
first means for measuring a first signal corresponding to the acceleration due to patient effort along a first axis;
second means for measuring a second signal corresponding to the acceleration due to patient effort along a second axis, wherein the first and second axes are perpendicular to one another and parallel to said flat surface of the pacemaker box; and
means for computing a control parameter for controlling the parameter stimulation frequency based on the first and second signals.

20. The apparatus of claim 19 wherein the computing means further comprises means for providing a third signal as a function of the first and second signals and means for integrating the third signal over a time period wherein the integrating means is highly constant in time and provides a digital output signal as the control parameter.

21. The apparatus of claim 20 wherein said integrating means comprises an integrator which generates a fast ramp signal in response to the third signal with a time constant of a few milliseconds, a reference voltage comparator having an input for a reference voltage and an input for the ramp signal input and an output that flips state in response to the ramp signal input reaching or exceeding the reference voltage, a monostable circuit having a pulse output in response to each flip of said comparator, and a counter for counting each pulse output during said time period, wherein the counter count provides the digital output signal.

22. The apparatus of claim 20 wherein said providing means further comprises means for providing the third signal as the sum of the absolute values of said first and second signals.

23. The apparatus of claim 20 wherein said providing means further comprises means for providing the third signal as the square root of the sum of the squares of said first and second signals.

24. The apparatus of claim 19 wherein the first and second measuring means further comprise a first accelerometric sensor having a capacitance that varies in response to motion along the first axis and a second accelerometric sensor having a capacitance that varies in response to motion along the second axis.

25. A method for providing a control parameter related to the effort of a patient for a pacemaker having a stimulation frequency controlled by the patient's effort, comprising:
providing a pacemaker box with a flat surface for implantation in a patient so that said flat surface is disposed in a vertical orientation;
measuring first and second signals corresponding to the acceleration, in response to patient effort, along first and second axes which are perpendicular to one another and parallel to said flat surface of the pacemaker box;
computing a control parameter based on the first and second signals; and
providing said control parameter for controlling the pacemaker stimulation frequency.

26. The method of claim 25 wherein computing said control parameter further comprises computing said control parameter as a function of the values of the signals representing the acceleration along said first and second axes, in relation to the metabolic power used up by the patient in the course of the effort producing said first and second signals.

27. The method of claim 26 wherein computing said control parameter function further comprises processing the first and second signals to produce a third signal, integrating the third signal over a time period, and providing the integrated third signal at the end of the time period in the form of a digital output signal as the control parameter.

28. The method of claim 27 wherein integrating the third signal further comprises generating a fast ramp signal in response to the third signal with a time constant of a few milliseconds, providing a reference voltage, comparing the ramp signal to the reference voltage, issuing a pulse each time the ramp signal reaches or exceeds the reference voltage, and counting each pulse during said time period, wherein the count provides the digital output signal.

29. The method of claim 27 wherein processing the first and second signals further comprises providing the sum of the absolute values of said first and second signals.

30. The method of claim 27 wherein processing the first and second signals further comprises providing the square root of the sum of the squares of said first and second signals.

31. The method of claim 25 wherein measuring said first and second signals further comprises sensing separately a capacity variation in response to acceleration in each axis.

32. A pacemaker having a frequency controlled by a patient's effort comprising:
a first accelerometer having a first signal corresponding to acceleration along a first axis;
a second accelerometer having a second signal corresponding to acceleration along a second axis;
a third accelerometer having a third signal corresponding to acceleration along a third axis, the first, second, and third axes being orthogonal;
means for computing a control parameter, representative of the patient's effort for varying the pacemaker frequency, as a function of the first, second, and third signals, said computing means further comprising means for summing the absolute values of the first, second, and third signals and means for integrating said sum over a time period and producing an output signals that is said integrated sum at the end of said time period, wherein the output signal represents said control parameter.

33. The pacemaker of claim 32 wherein said integrating means output signal is said control parameter in digital form.

34. The pacemaker of claim 32 wherein said integrating means further comprises:
a generator having a ramp signal output and a time constant, the time constant being less than the time period;
means for comparing the ramp generator output to a reference threshold and flipping states when the ramp generator output rises to the reference threshold;
a monostable circuit connected to the comparator output, said monostable circuit generating a pulse in response to a flip of the comparator means; and
a counter that response to a pulse generated by the monostable circuit, wherein the counter counts the number of pulses generated during the time period, said count output at the end of the time period being the control parameter in digital form.

35. The pacemaker of claim 34 further comprising a processing means for receiving said output count at the end of the time period and determining the pacing frequency as a function of said count.

36. A pacemaker having a stimulation frequency controlled by a control parameter related to the patient's effort comprising:
a first accelerometer that is sensitive to motion in one direction having a first signal output corresponding to acceleration along a first axis;
a second accelerometer that is sensitive to motion in one direction having a second signal output corresponding to acceleration along a second axis, the first and second axes being perpendicular;
wherein the first and second accelerometers are each comprised of a flat substratum disposed in a plane such that the one direction of sensitivity is contained in said substratum plane; and
means for computing a control parameter, representative of the patient's effort for varying the pacemaker frequency, as a function of the first and second signals.

37. The pacemaker of claim 36 wherein each of the first and second accelerometers has a capacitance that varies in response to motion in said one direction.

38. The pacemaker of claim 36 wherein in the first and second accelerometers further comprise the same substratum such that the one directions of the two accelerometers are perpendicular and contained in said same substratum plane.

39. The pacemaker of claim 38 wherein each of the first and second accelerometers has a capacitance that varies in response to motion in said one direction.

40. The pacemaker of claim 36 wherein the computing means further comprises means for summing the absolute values of the first and second signals, and means for integrating said sum over a time period and producing an output signal that is said integrated sum at the end of said time period, wherein the output signal is said control parameter.

41. The pacemaker of claim 40 wherein each of the first and second accelerometers has a capacitance that varies in response to motion in said one direction.

42. The pacemaker of claim 40 wherein said integrating means further comprises:
a generator having an input for said sum signal, a ramp signal output and a time constant, the time constant being less than the time period;
means for comparing the ramp generator output to a reference threshold and flipping states when the ramp generator output rises to the reference threshold;
a monostable circuit connected to the comparator output, said monostable circuit generating a pulse in response to a flip of the comparator means; and
a counter that responds to a pulse generated by the monostable circuit, wherein the counter counts the number of pulses generated during the time period, said count output at the end of the time period being the control parameter in digital form.

43. The pacemaker of claim 36 wherein the computing means further comprises means of taking the square root of the sum of the squares of the first and second signals, and means for integrating said square root over a time period and producing an output signal that is said integrated square root at the end of said time period, wherein the output signal is said control parameter.

44. The pacemaker of claim 43 wherein each of the first and second accelerometers has a capacitance that varies in response to motion in said one direction.

45. The pacemaker of claim 36 further comprising:
a third accelerometer that is sensitive to motion in one direction having a third signal output corresponding to acceleration along a third axis, the third axis being perpendicular to the first and second axes;
wherein the third accelerometer is comprised of a flat substratum disposed in a plane such that the one direction of sensitivity is contained in said substratum plane; and
wherein said computing means computes said control parameter as a function of the first, second and third signals.

46. The pacemaker of claim 45 wherein each of the first, second and third accelerometers has a capacitance that varies in response to motion in said one direction.

47. The pacemaker of claim 45 wherein two of the first, second and third accelerometers further comprise the same substratum such that the one directions of the said two accelerometers are perpendicular and contained in said same substratum plane.

48. The pacemaker of claim 46 wherein each of the first, second and third accelerometers has a capacitance that varies in response to motion in said one direction.

49. The pacemaker of claim 45 wherein the computing means further comprises means or summing the absolute values of the first, second and third signals and means for integrating said sum over a time period and producing an output signal that is said integrated sum at the end of said time period, wherein the output signal represents said control parameter.

50. The pacemaker of claim 45 wherein the computing means further comprises means for taking the square root of the sum of the squares of the first, second, and third signals, and means for integrating said square root over a time period and producing an output signal that is said integrated square root at the end of said time period, wherein the output signal represents said control parameter.

51. A method for calculating a control parameter related to a patient's effort for use in controlling the stimulation frequency of a pacemaker comprising:
a) measuring first and second signals corresponding to the acceleration along first and second axes which are perpendicular to one another;
b) providing the sum of the absolute values of the first and second signals as a third signal; and
c) integrating the third signal over a time period and providing said integrated third signal as the control parameter, wherein the control parameter is used to control the stimulation frequency of a pacemaker.

52. The method of claim 51 wherein step c) further comprises providing said integrated third signal in digital form.

53. The method of claim 51 wherein step c) further comprises:
providing a time constant and a reference threshold, the time constant being less than the time period;
generating a ramp signal output in response to said third signal and said time constant;
comparing the ramp signal output to the reference threshold;
indicating when the ramp signal output rises to the threshold and resetting the ramp signal output;
counting the number of times the ramp signal output rises to the threshold during the time period, wherein said count output at the end of the time period represents the control parameter in digital form.

54. The method of claim 53 comprising processing the count output at the end of the time period and determining the pacing frequency as a function of said count.

55. A method for calculating a control parameter related to a patient's effort for use in controlling the stimulation frequency of a pacemaker, comprising:
a) providing first and second accelerometric sensors, each being comprised of a flat substratum and sensitive in one direction contained in the plane of said substratum, wherein the one direction of the first accelerometric sensor and the one direction of the second accelerometric sensor are perpendicular;
b) sensing the output of the first and second accelerometric sensors as first and second signals;
c) processing the first and second signals to form a third signal as a function of the first and second signals, said function being related to the patient's effort producing the first and second signals; and
d) integrating the third signal over a time period and providing said integrated third signal as a control parameter, wherein the control parameter is used to control the stimulation frequency of a pacemaker.

56. The method of claim 55 wherein step a) further comprises providing each of the first and second accelerometers with a capacity variation in response to motion in said one direction.

57. The method of claim 55 wherein step a) further comprises forming the first and second accelerometers in the same substratum such that the one directions of the two accelerometers are perpendicular and contained in said same substratum plane.

58. The method of claim 57 wherein step a) further comprises providing each of the first and second accelerometers with a capacity variation in response to motion in said one direction.

59. The method of claim 55 wherein step c) further comprises summing the absolute values of the first and second signals, and wherein step d) further comprises integrating said sum over the time period to produce said control parameter.

60. The method of claim 59 wherein step a) further comprises:
providing each of the first and second accelerometers with a capacity variation in response to motion in said one direction; and
forming the first and second accelerometers in the same substratum such that the one directions of the two accelerometers are perpendicular and contained in said same substratum plane.

61. The method of claim 59 wherein step d) further comprises:
providing a time constant and a reference threshold, the time constant being less than the time period;

generating a ramp signal output in response to said sum and said time constant;

comparing the ramp signal output to the reference threshold;

indicating when the ramp signal output rises to the reference threshold and resetting the ramp signal output;

counting the number of times the ramp signal output rises to the reference threshold during the time period, wherein said count output at the end of the time period is the control parameter in digital form.

62. The method of claim 55 wherein step c) further comprises taking the square root of the sum of the squares of the first and second signals, and wherein step d) integrates said square root over said time period to produce said control parameter.

63. The method of claim 62 wherein step a) further comprises:

providing each of the first and second accelerometers with a capacity variation in response to motion in said one direction; and forming the first and second accelerometers in the same substratum such that the one directions of the two accelerometers are perpendicular and contained in said same substratum plane.

64. The method of claim 63 wherein step d) further comprises:

providing a time constant and a reference threshold, the time constant being less than the time period;

generating a ramp signal output in response to said sum;

comparing the ramp signal output to the reference threshold;

indicating when the ramp signal output rises to the reference threshold and resetting the ramp signal output;

counting the number of times the ramp signal output rises to the reference threshold during the time period, wherein said count output at the end of the time period is the control parameter in digital form.

65. The method of claim 55, further comprising:

providing a third accelerometric sensor comprised of a flat substratum and sensitive in one direction contained in the plane of said substratum;

orienting the one direction of the third accelerometric sensor perpendicular to the one directions of the first and second accelerometric sensors;

sensing the output of the third accelerometric sensor as a fourth signal; and wherein step c) further comprises processing the first, second and fourth signals to form said third signal as a function of the first, second and fourth signals.

66. The method of claim 65 wherein step a) further comprises providing each of the first, second and third accelerometers with a capacity variation in response to motion in said one direction.

67. The method of claim 65 wherein step a) further comprises forming two of the first, second and third accelerometers in the same substratum such that the one directions of the two accelerometers are perpendicular and contained in said same substratum plane.

68. The method of claim 67 wherein step a) further comprises providing each of the first, second and third accelerometers with a capacity variation in response to motion in said one direction.

69. The method of claim 65 wherein step c) further comprises summing the absolute values of the first, second and fourth signals and wherein step d) further comprises integrating said sum over said time period.

70. The method of claim 65 wherein step c) further comprises taking the square root of the sum of the squares of the first, second, and fourth signals, and wherein step d) further comprises integrating said square root over said time period.

* * * * *

UNITED STATES PATENT AND TRADEMARK OFFICE
CERTIFICATE OF CORRECTION

PATENT NO. : 5,330,510
DATED : July 19, 1994
INVENTOR(S) : Legay et al.

It is certified that error appears in the above-indentified patent and that said Letters Patent is hereby corrected as shown below:

Column 3, line 10, after "motion" should be --,--;

Column 6, line 10, "computer" should be --computed--;

Column 7, line 24, "15" should be --10--;

Column 7, line 32, "comprising" should be "comprises";

Column 7, line 55, "an" should be --and--;

Column 11, line 33, "46" should be --47--.

Signed and Sealed this

Eighth Day of August, 1995

Attest:

BRUCE LEHMAN

Attesting Officer

Commissioner of Patents and Trademarks